United States Patent
Zhao (10) Patent No.: US 11,737,772 B2
(45) Date of Patent: Aug. 29, 2023

(54) NASAL PLUG

(71) Applicant: Ohio State Innovation Foundation, Columbus, OH (US)

(72) Inventor: Kai Zhao, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 794 days.

(21) Appl. No.: 16/491,958

(22) PCT Filed: Mar. 8, 2018

(86) PCT No.: PCT/US2018/021464
§ 371 (c)(1),
(2) Date: Sep. 6, 2019

(87) PCT Pub. No.: WO2018/165372
PCT Pub. Date: Sep. 13, 2018

(65) Prior Publication Data
US 2020/0069321 A1 Mar. 5, 2020

Related U.S. Application Data

(60) Provisional application No. 62/468,665, filed on Mar. 8, 2017.

(51) Int. Cl.
*A61B 17/24* (2006.01)
*A61B 17/00* (2006.01)
(Continued)

(52) U.S. Cl.
CPC ........ *A61B 17/24* (2013.01); *A61B 17/12036* (2013.01); *A61B 17/12104* (2013.01);
(Continued)

(58) Field of Classification Search
CPC .......... A61F 5/08; A61F 5/56; A61F 13/2005; A61F 13/2042; A61F 11/085; A61F 1/08;
(Continued)

(56) References Cited

U.S. PATENT DOCUMENTS 2,569,743 A * 10/1951 Carlock .................... A61F 5/56
606/199
3,935,859 A * 2/1976 Doyle ................ A61F 5/05891
606/199
(Continued)

FOREIGN PATENT DOCUMENTS

CN 102949769 A 3/2013
WO 2014/104066 A1 7/2014

OTHER PUBLICATIONS

International Search Report and Written Opinion issued by the International Searching Authority (ISA/RU) in PCT Application No. PCT/US2018/021464 dated Jun. 28, 2018. 7 pages.
(Continued)

*Primary Examiner* — Kathleen S Holwerda
*Assistant Examiner* — Serenity A Miller
(74) *Attorney, Agent, or Firm* — Meunier Carlin & Curfman LLC (57) ABSTRACT

The present invention relates to a nasal plug for diverting airflow from a natural flow path in a person's nostril. In some circumstances, the airflow is channeled and directed to a specific location in a person's nasal or sinus cavity. The person may adjust and self-select a preferred airflow path by adjusting the nasal plug's location in the nostril, e.g., rotating the plugs. A kit may include two plugs, which may be used singly or in combination with each other and are independently adjustable/rotatable. A method for reducing nasal discomfort or improving nasal functions by diverting channeled airflow in a nostril is also disclosed.

19 Claims, 9 Drawing Sheets

(51) Int. Cl.
*A61F 5/08* (2006.01)
*A61B 17/12* (2006.01)

(52) U.S. Cl.
CPC .... *A61B 17/12159* (2013.01); *A61B 17/1204* (2013.01); *A61B 2017/00862* (2013.01); *A61F 5/08* (2013.01)

(58) Field of Classification Search
CPC ....... A61F 5/05891; A61M 2210/0618; A61M 16/0666; A62B 23/06; A61B 17/24; A61B 2017/248; A61B 2017/246
USPC .......................................................... 128/887
See application file for complete search history.

(56) References Cited

U.S. PATENT DOCUMENTS

| | | | | |
|---|---|---|---|---|
| 5,105,807 | A * | 4/1992 | Kahn | A61M 25/02 128/911 |
| 5,425,359 | A | 6/1995 | Nan-Tien | |
| 5,601,594 | A * | 2/1997 | Best | A61F 5/08 606/199 |
| 6,478,026 | B1 * | 11/2002 | Wood | A61M 16/1055 128/207.18 |
| 6,561,188 | B1 * | 5/2003 | Ellis | A62B 23/06 128/207.18 |
| 6,561,193 | B1 | 5/2003 | Noble | |
| 6,848,446 | B2 * | 2/2005 | Noble | A61M 16/0666 128/207.18 |
| 7,506,649 | B2 | 3/2009 | Doshi et al. | |
| 7,856,979 | B2 * | 12/2010 | Doshi | A61F 5/08 128/850 |
| 8,517,022 | B2 * | 8/2013 | Halling | A61M 16/0666 128/206.11 |
| 2004/0059368 | A1 | 3/2004 | Maryanka | |
| 2009/0194100 | A1 | 8/2009 | Minagi | |
| 2009/0308398 | A1 | 12/2009 | Ferdinand | |
| 2012/0046607 | A1 | 2/2012 | Syk | |

OTHER PUBLICATIONS

Uldry, et al., Sniff nasal inspiratory pressure in patients with chronic obstructive pulmonary disease. Eur Respir J 1997; 10: 1292-1296.
Heritier, et al., Sniff nasal inspiratory pressure. A noninvasive assessment of inspiratory muscle strength. Am J Respir Crit Care Med vol. 150. 1994, pp. 1678-1683.
Zhao, Kai, et al. "Perceiving nasal patency through mucosal cooling rather than air temperature or nasal resistance." PLoS One 6.10 (2011): e24618.
International Preliminary Report on Patentability Issued for Application No. PCT/US2018/021464, dated Sep. 19, 2019.

* cited by examiner

(iii)

(iii)

NASAL PLUG

STATEMENT OF GOVERNMENT SUPPORT

This invention was made with government support under grant number DC013626 awarded by the National Institutes of Health. The government has certain rights in the invention.

BACKGROUND OF THE INVENTION

Field of the Invention

Embodiments of the present invention relate to nasal plug, specifically a nasal plug perforated by a tube or an air channel.

Background

Nasal sinus disease is one of the most common medical conditions in the US, affecting an estimated 13% of adults, or some 30 million people. It accounts for 12.5 million physician office visits each year and an annual health expenditure of $5.8 billion (National Health Interview Survey 2009, CDC). It significantly impacts patient quality of life, even comparable to that of chronic debilitating diseases such as diabetes and congestive heart failure. Among its many symptoms, complaints of nasal obstruction is one of the primary symptoms that most significant impact a patient's quality of life. Many patients' nasal airflow patterns are disoriented, e.g. forming into a narrow jet. In fact, it is well known that patients' perception of nasal obstruction does not correlate to their nasal resistance, and could be due to irregular perception of nasal airflow, as discussed in "Perceiving Nasal Patency through Mucosal Cooling Rather than Air Temperature or Nasal Resistance," Zhao et al., PLoS ONE, Vol. 6, Issue 10, October 2011.

For example, Empty Nose Syndrome (ENS) is a rare but debilitating disease that occur after surgical therapy that supposedly treating their nasal sinus problems. Rather, following surgery, patients would have wide nasal airway (no obstruction), but still paradoxically complain of nasal obstruction. Other symptoms, including nasal crusting, dryness, nasal discharge, and nasal pain often accompany, or replace nasal obstruction. This syndrome can have a devastating impact on patients' quality of life: constant feeling of suffocation, elevated anxiety, disrupted concentration, chronic hyperventilation, chronic fatigue, severe sleeping difficulty and psychological disorders. Patients have committed suicide and committed murder on their physician as the results of the symptoms.

Accordingly, there is a need for treatment and relief of a person's perceived symptom of nasal obstruction beyond nasal resistance.

Figure 1:
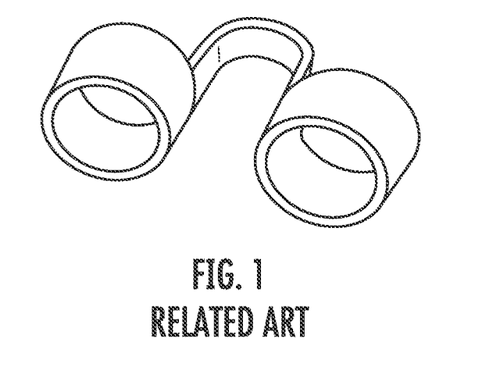
FIG. 1 illustrates a related art nasal dilator.

Prior art nasal plugs do not address the issues with disoriented nasal airflow patterns as well as empty nose syndrome because they are designed to merely prop open or dilate the nostrils. As illustrated in FIG. 1, a commercial nasal dilator includes two rigid cylindrical rings connected by a bridge. Each cylindrical ring provides a non-directional air flow and may, in fact, open the nasal passage to allow more airflow than "baseline" (non-dilated) because it props open the nares more than baseline. Even if pliable, these dilators do not serve to direct air flow.

BRIEF SUMMARY OF THE INVENTION

Accordingly, the present invention is directed to nasal plug that obviates one or more of the problems due to limitations and disadvantages of the related art.

An advantage of the present invention is to provide a nasal plug having a pliable insert having a first surface and a second surface, a cross-section of the pliable insert sized to be accepted into and to fluidically seal a person's nasal nare, the pliable insert having an axis therethrough from the first surface to the second surface; and a passage through the pliable insert from the first surface to the second surface, the passage having a distal end and a proximal end, wherein the proximal end of the passage is offset from the axis by an angle $\alpha$, where $\alpha > 0°$.

In another aspect of the present invention, further embodiment of a method of treating nasal discomfort and improving nasal function in a person, the method comprising channeling airflow through one nostril of a person; and diverting the channeled airflow through the one nostril, thereby modulating the natural flow path in the one nostril.

In another aspect of the present invention, a kit for reducing nasal discomfort include a first nasal plug comprising a first pliable insert having a first surface and a second surface, a cross-section of the pliable insert sized to be accepted into and to fluidically seal a person's nasal nare, the first pliable insert having a first axis therethrough from the first surface to the second surface; and a first passage through the first pliable insert from the first surface to the second surface, the passage having a distal end and a proximal end, wherein the proximal end of the passage is offset from the axis by an angle $\alpha$, where $\alpha > 0°$; and a second nasal plug comprising a second pliable insert having a first surface and a second surface, a cross-section of the pliable insert sized to be accepted into and to fluidically seal a person's nasal nare, the pliable insert having a second axis therethrough from the first surface to the second surface; and a passage through the pliable insert from the first surface to the second surface, the passage having a distal end and a proximal end, wherein the proximal end of the passage is offset from the second axis by an angle $\alpha$, where $\alpha > 0°$; wherein the first nasal plug and the second nasal plug are independent from one another such that the first axis and the second axis are capable of extending in different orientations Further embodiments, features, and advantages of the nasal plug, as well as the structure and operation of the various embodiments of the nasal plug, are described in detail below with reference to the accompanying drawings.

It is to be understood that both the foregoing general description and the following detailed description are exemplary and explanatory only and are not restrictive of the invention as claimed.

BRIEF DESCRIPTION OF THE DRAWINGS

The accompanying figures, which are incorporated herein and form part of the specification, illustrate nasal plugs according to principles of the present invention. Together with the description, the figures further serve to explain the principles of the nasal plug described herein and thereby enable a person skilled in the pertinent art to make and use the nasal plug.

FIG. 5A (i) is a view of the location of the tubes in a person's nares in a "down" position; FIG. 5A (ii) is an illustration of the positioning of the tube exit in a person's nares in the "down" position; FIG. 5A (iii) is a side view of the patient with a nasal plug with the tube in the "down" position. "Down" refers to the airflow being directed to a lower portion of the nasal cavity of the patient.

FIG. 5B (i) is a view of the location of the tubes in a person's nares in a "up" position; FIG. 5B (ii) is an illustration of the positioning of the tube exit in a person's nares in the "up" position; FIG. 5B (iii) is a side view of a person with a nasal plug with the tube in the "up" position. "Up" refers to the airflow being directed to an upper portion of the nasal cavity.

DETAILED DESCRIPTION OF THE INVENTION

Reference will now be made in detail to embodiments of the nasal plug with reference to the accompanying figures. It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The mechanisms leading to perception of nasal obstruction by patients with nasal sinus disease remain poorly understood. Subjective complaints often bear little relationship to the actual physical resistance to airflow in the nose. Altered nasal aerodynamics is often suspected as a major contributing factor. Our study has shown that, as an extreme example, for all ENS patients that were seen in our clinic, previous surgeries that opened up the nasal airway, resulted paradoxically in nasal airflow forming into a narrow jet towards the middle meatus region, leaving the other airway with significantly reduced airflow. The over-congregated nasal airflow may over stress a small patch of the nasal mucosa resulting in excessive nasal dryness or crusting of which many ENS patients complained. It will also reduce the capacity of the nasal mucosal to detect airflow.

Figure 2:
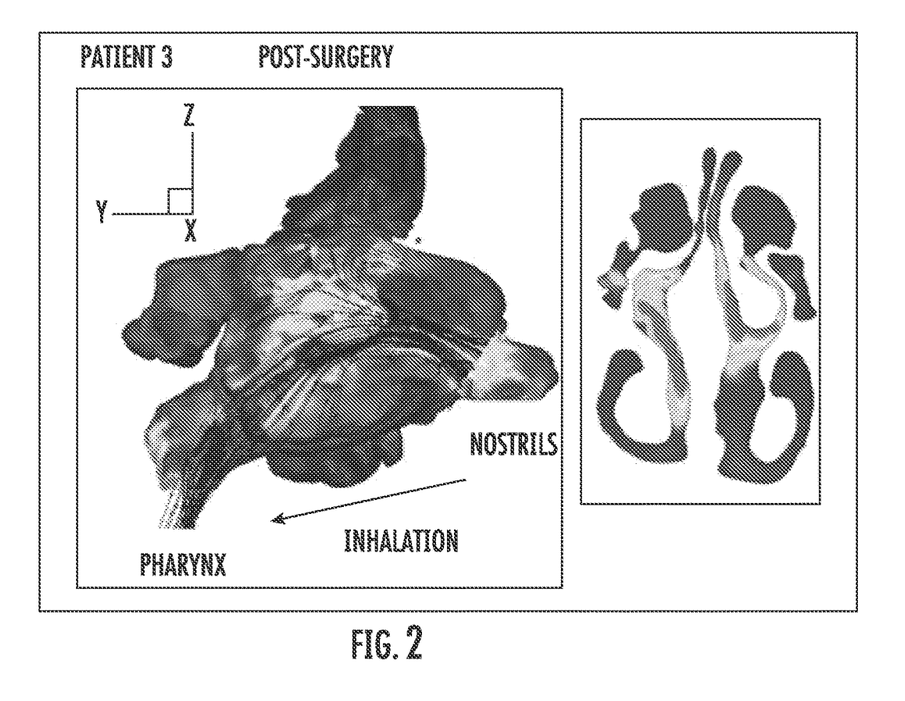
FIG. 2 illustrates nasal air flow in a patient's sinus cavity.

Referring to FIG. 2, according to principles of the present invention, the nasal flow in the patient is directed away from the red (high flow) zone and into the blue (low flow) zone to potentially alleviate patient's symptoms.

Figure 3:
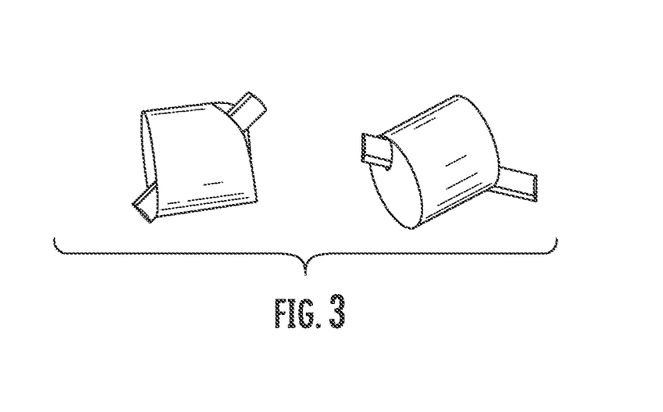
FIG. 3 shows an embodiment of the nasal plug according to principles of the present invention.

As illustrated in FIG. 3, a nasal plug according to principles of the present invention includes a pliable "plug", as shown, a cylindrical profile, shaped to adapt to a nostril or nasal nare of a patient so as to substantially seal air flow. That is, the nasal plug itself, without further modification, would substantially cause the patient to be unable to breathe through a nostril into which it is inserted. As such, the actual profile of the nasal plug could be of any shape sufficient to block air flow, and such profile may dependent on the pliability of the nasal plug material. For example, if the nasal plug is made of a soft pliable foam, as illustrated in FIG. 3, then the profile may be cylindrical, but could also be angular, e.g., rectangular, square, triangular or could be oval, spherical, or other shape suitable to block air passage through the nostril but for a passage according to principles of the present invention. The nasal plug may be made of foam, silicon or any other soft material That is, a passage is provided through the nasal plug from a distal end of the plug to a proximal end of the plug, where distal is used herein to be the portion of the plug that is external to a person once the plug is inserted into the person's nostril. The passage may include a tube or other support structure there through to provide additional stability and to maintain the passage or bore through the nasal plug. Such support structure can be integral or fixedly attached to the interior of the nasal plug passage or may be held in place by other methods, such as interference fit or friction fit, or may even be held in place by an adhesive. The tubes may be made of plastic or any material that can maintain the shape and structure. Although illustrated as cylindrical, the tube may be of any shape that provides appropriate airflow through the passage, such as conical or squares.

Figure 4:
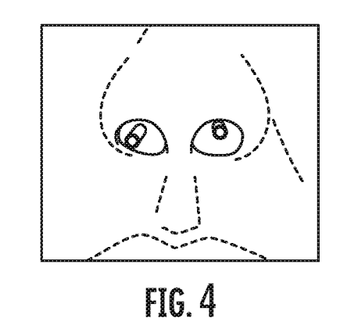
FIG. 4 shows the nasal plug of FIG. 2 as worn by a patient.
Figure 14:
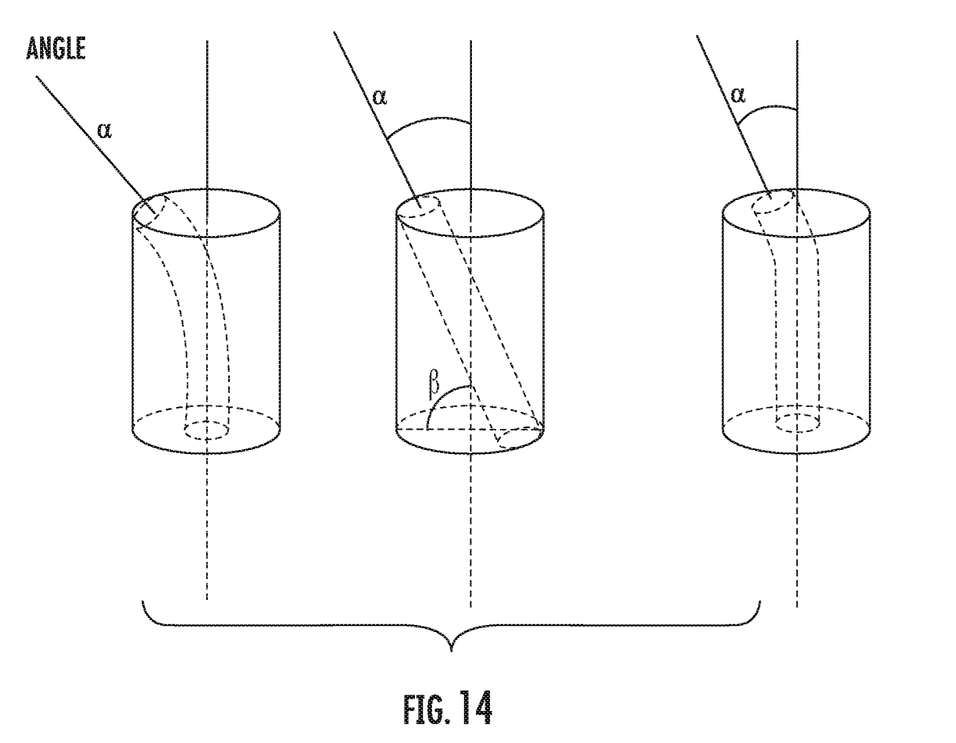
FIG. 14 illustrates exemplary embodiments of the tube or passage through the nasal plug.

As illustrated in FIGS. 3 and 4, an embodiment of the nasal plug according to principles of the present invention includes two parts: a nasal plug of pliable material having a passage there through and a tube in the passage. A nasal plug of this configuration is applied to each nostril of a patient. The tube passing through the nasal plug, or the passage without the tube, has a predetermined angle with respect to an axial direction of the nasal plug to provide airflow to the nostril at a predetermined location within the sinuses. In the alternative of the entire tube or passage being at an angle through the entire length of the nasal plug, a portion of the tube or passage may be angled to provide an exit at the proximate end of the nasal plug at the appropriate predetermined angle α. In an aspect, the passage may extend from the first surface to the second surface at an angle β of approximately 30° with respect to the first surface. Various embodiments of the tube or passage with an exit portion at a predetermined angle to the axial direction of the plug are illustrated in FIG. 14.

The predetermined angle α may be different or the same for different nostrils in the same patient. For example, the angle may be >20° from a central axis (axial direction) of the nasal plug. The angle may range from about 5° to 70°. For example, the nasal foam plugs with embedded tubes illustrated in FIGS. 3 and 4, which shows a patient with nasal plugs according to principles of the present invention, would re-direct nasal airflow to different directions. At least in some circumstances, the angle should be determined such that the air flow through the passage is directed to a person's lower meatus. That is, the angle of the passage may be in the range of >5°, and in some circumstances, >10°.

Although not shown in the figures, a nasal foam plug according to principles of the present invention may be a single piece for use in both nostrils of a patient. That is, the foam plug may be a single unit with two passages there through, each passage positioned to be enter one of the person's nostrils. This unitary nasal plug may include tubes or other a support structure through each passage to provide additional stability and to maintain the passage or bore through the nasal plug. Such support structure can be integral or fixedly attached to the interior of the nasal plug passage or may be held in place by other methods, such as interference fit or friction fit, or may even be held in place by an adhesive. Although illustrated as cylindrical, the tube may be of any shape that provides appropriate airflow through the passage.

According to principles of the present invention, nasal plugs address the problem that some people's nasal airflow patterns are severely disoriented, e.g. forming into a narrow jet towards the middle meatus. The nasal plug described herein redirects the nasal flow in these patients to mimic normal nasal airflow patterns. That is, the airflow through the passage may be directed to the lower meatus, thus mimicking healthy airflow.

Figure 5A:
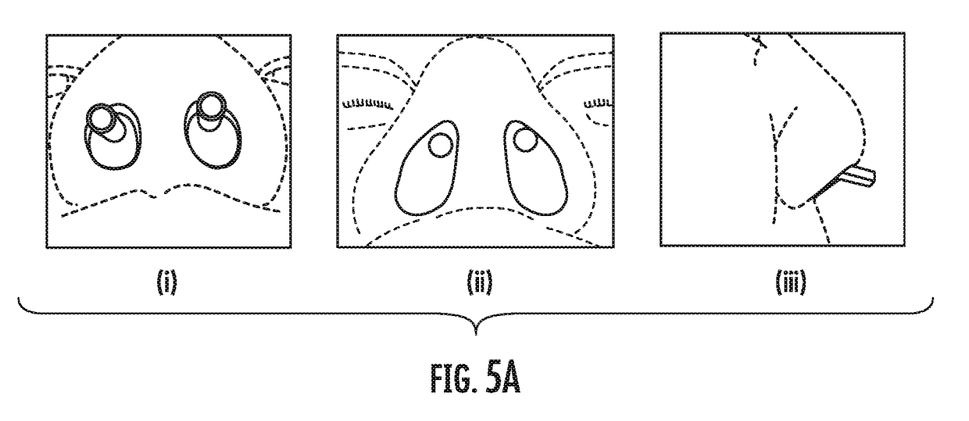
Figure 5B:
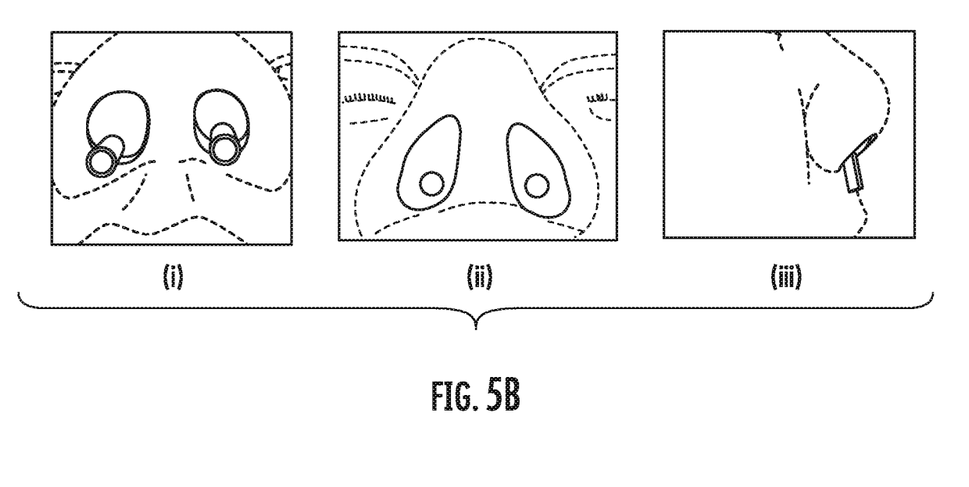

As illustrated in FIGS. 5A and 5B, the nasal plugs may be independently adjusted by the user to provide the best sensation of airflow. Turning or adjusting the plugs changes the angle at which the directed airflow enters the sinus cavity. Each of FIG. 5A and FIG. 5B shows a single user with the nasal plugs in both nostrils adjusted to the same angle. However, because the nasal plugs are independent, the user is not limited to having the same angle of orientation in both nostrils of the same user.

FIG. 5A illustrates a "down" orientation of the airflow in which "down" refers to the airflow being directed to a lower portion of the nasal cavity of the patient. FIG. 5B illustrates an "up" orientation of the air flow in which "up" refers to the airflow being directed to an upper portion of the nasal cavity. While these two "orientations" are illustrated, the patient may find that and different orientation between "down" and "up" will provide the best sensation of airflow. The "down" orientation and the "up" orientation were tested in a patient, and the patient evaluated the sensation in the nasal cavity.

FIG. 5A (i) is a view of the location of the tubes in a person's nares in a "down" position; FIG. 5A (ii) is an illustration of the positioning of the tube exit in a person's nares in the "down" position; FIG. 5A (iii) is a side view of the patient with a nasal plug with the tube in the "down" position.

FIG. 5B (i) is a view of the location of the tubes in a person's nares in a "up" position; FIG. 5B (ii) is an illustration of the positioning of the tube exit in a person's nares in the "up" position; FIG. 5B (iii) is a side view of a person with a nasal plug with the tube in the "up" position.

Figure 6A:
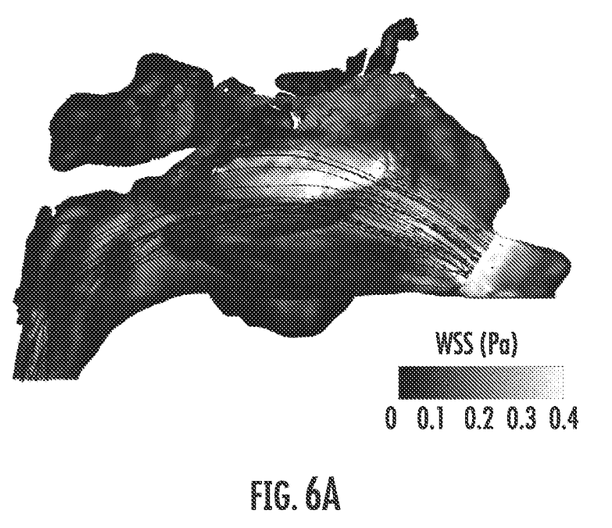
FIG. 6A illustrates what is considered a natural airflow in the nasal cavity.
Figure 6B:
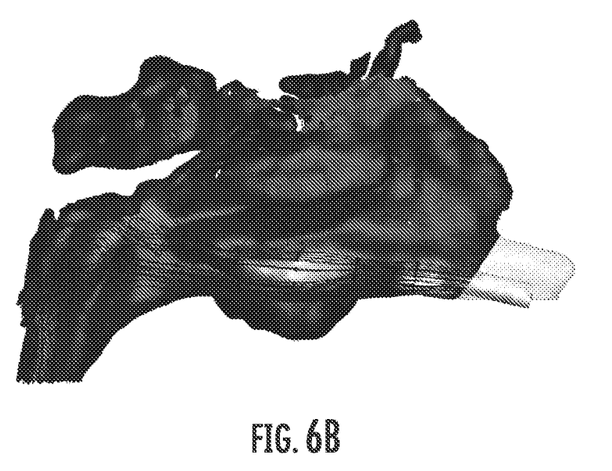
FIG. 6B illustrates airflow in the nasal cavity when a patient uses a nasal plug according to principles of the present invention with the tube in the "down" position, as shown in FIG. 5A.
Figure 6C:
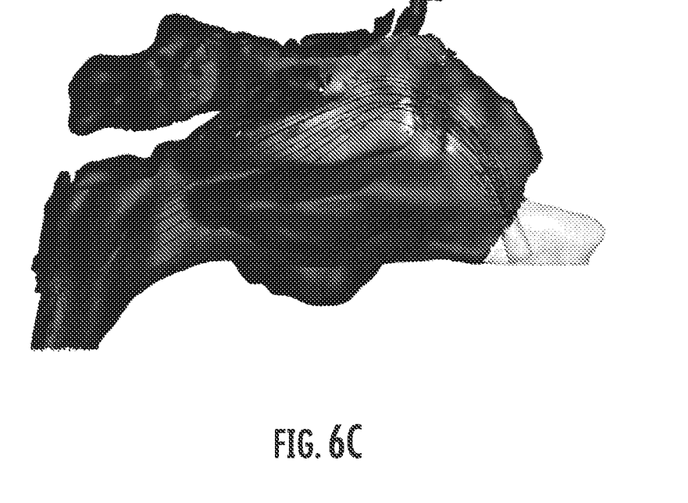
FIG. 6C illustrates airflow in the nasal cavity when a patient uses a nasal plug according to principles of the present invention with the tube in the "up" position, as shown in FIG. 5B.

FIG. 6A illustrates what is considered an irregular airflow in the nasal cavity of an exemplary patient. FIG. 6B illustrates airflow in the nasal cavity when the exemplary patient uses a nasal plug according to principles of the present invention with the tube in the "down" position, as shown in FIG. 5A. FIG. 6C illustrates airflow in the nasal cavity when the patient uses a nasal plug according to principles of the present invention with the tube in the "up" position, as shown in FIG. 5B. FIGS. 6A-C illustrate the airflow pathways and the wall shear stress (WSS) exerted by the airflow on the nasal passages in pascals. A legend for determining the WSS in each of FIGS. 6A-C is provided in FIG. 6A.

Inventors performed a test of the nasal plugs illustrated in the FIGS. 5A and 5B in the exemplary patient, with the plugs in the "down" position for 5 minutes and with the plugs in the "up" position for 5 mins. The exemplary patient was then asked to rotate or reposition each of the plugs to adjust the angle of the airflow direction to a personalized "best" position that would make the patient "most" comfortable. The exemplary patient was asked complete the standard Empty Nose Syndrome 6-Item Questionnaire (ENS6Q), which asks patients to evaluate 6 common ENS symptoms (nasal suffocation, nasal burning, nasal openness, crusting, dryness, and impaired air sensation through nasal cavities). In the ENS6Q, the patients rate their symptoms according to the scale provided in Table 1, below.

TABLE 1

| | Please consider the SEVERITY of each problem in your rating | | | | | |
|---|---|---|---|---|---|---|
| | No problem | Very mild | Mild | Moderate | Severe | Extremely severe |
| Dryness | 0 | 1 | 2 | 3 | 4 | 5 |
| Sense of diminished nasal airflow (unable to breath/obstruction) | 0 | 1 | 2 | 3 | 4 | 5 |
| Suffocation | 0 | 1 | 2 | 3 | 4 | 5 |
| Nose feels too open | 0 | 1 | 2 | 3 | 4 | 5 |
| Nasal Crusting | 0 | 1 | 2 | 3 | 4 | 5 |
| Nasal Burning/Pain | 0 | 1 | 2 | 3 | 4 | 5 |

Figure 7A:
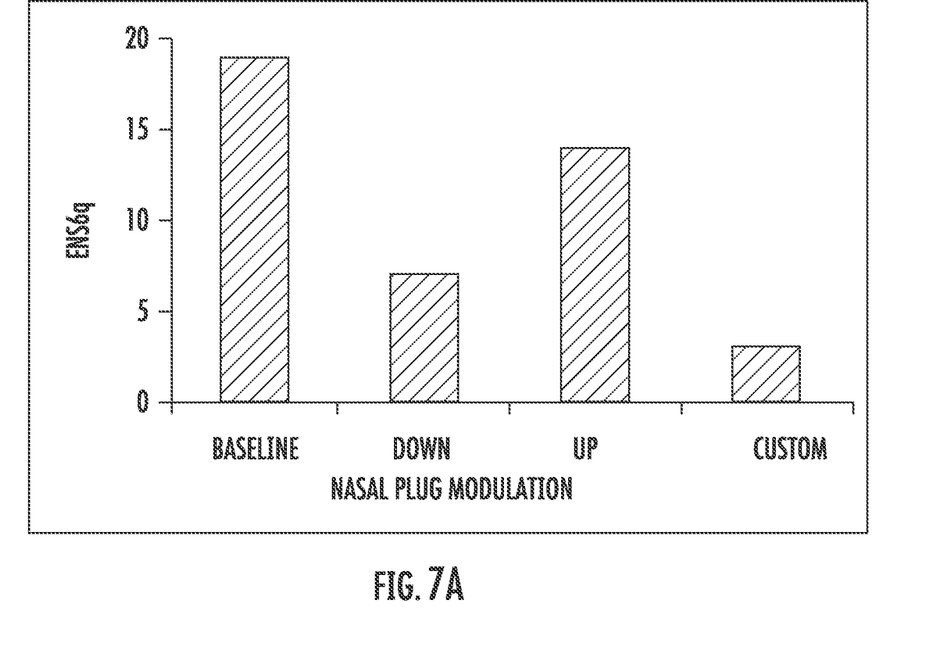
FIG. 7A shows the results of the exemplary patients ENS6Q scoring, where a lower cumulative score indicates a lower degree of symptoms, (e.g., 0 would be asymptomatic) and a higher cumulative score indicates a higher degree of symptoms (e.g., 20 would be highly symptomatic) for baseline, "down", "up" and "self-select" (i.e., custom) orientation of the nasal plug.
Figure 7B:
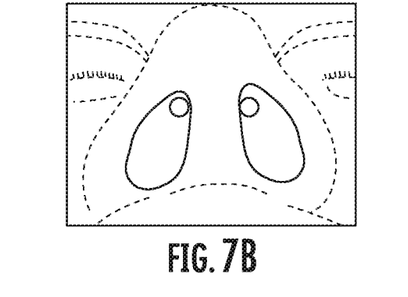
FIG. 7B illustrates the positioning of the tubes in the exemplary patient's nares at the custom position.

The exemplary patient's ENS6Q score for the baseline (without nasal plugs), with the nasal plug's both in the "down" position, with both the nasal plug's in the "up" position, and each nasal plug independently in a custom position established by the patient. FIG. 7A shows the results of the exemplary patients ENS6Q scoring, where a lower cumulative score indicates a lower degree of symptoms, (e.g., <11 would be asymptomatic) and a higher cumulative score indicates a higher degree of symptoms (e.g., 20 would be highly symptomatic). FIG. 7B illustrates the positioning of the tubes in the exemplary patient's nares at the custom position. It is worth noting that the exemplary patient commented about the relief provided by the nasal plugs according to principles described herein. "I cannot believe how much these things return the sensation of air! It is even more remarkable how much the sensation of air is diminished by rotating the plugs! You guys are undeniably onto something here."

Figure 8A:
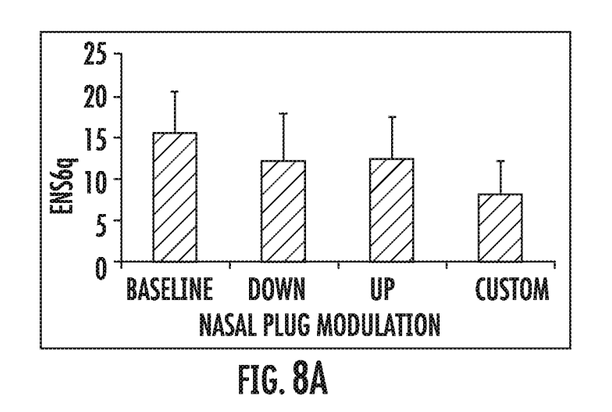
FIG. 8A shows Empty Nose Syndrome 6-Item Questionnaire (ENS6Q) for a sample of 12 patients.
Figure 8B:
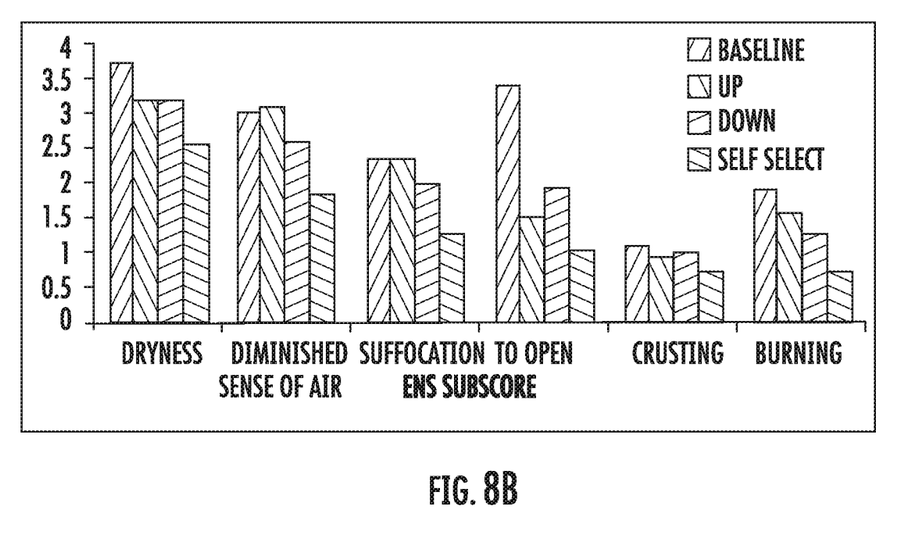
FIG. 8B, shows ENS6Q subscores of the six symptoms listed, the bar graphs are in the order "baseline", "up", "down" and "self-select" (i.e., custom).
Figure 8C:
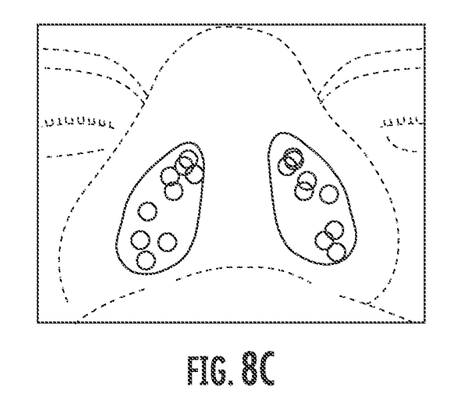
FIG. 8C is a "map" showing the study participants' custom (or self-select) locations for the independently positionable nasal plugs/tubes with respect to the nares that provided best self-perceived outcome.

A study of 12 patients was conducted using the nasal plugs as shown and described herein. In particular, prototypes of the type shown in FIG. 3 were provided to each of the 12 patients. The ENS6Q results for those patients is shown in FIG. 8A. A breakdown of the ENS6Q questions for the 12 patients is shown in FIG. 8B, where for each of the six symptoms listed, the bar graphs are in the order "baseline", "up", "down" and "self-select" (i.e., custom). FIG. 8C is a "map" showing the study participants' custom (or self-select) locations and angles for the independently positionable nasal plugs/tubes with respect to the nares.

Figure 9A:
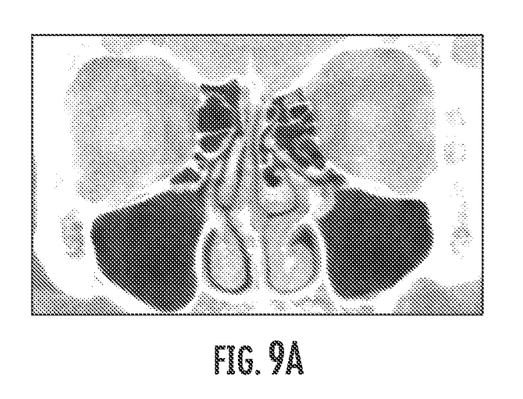
FIG. 9A shows the nasal cavity of an exemplary patient with turbinate hypertrophy.
Figure 9B:
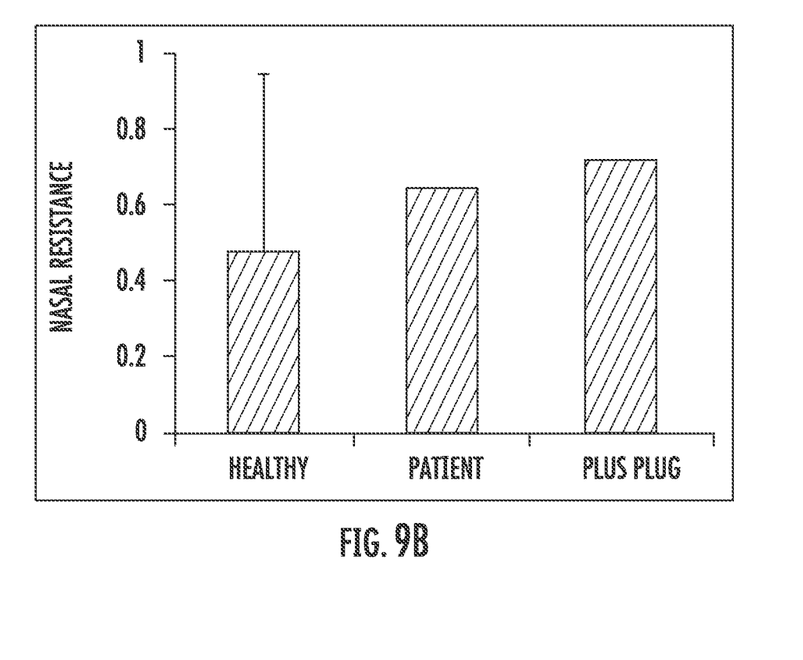
FIG. 9B illustrates the degree of nasal resistance in averaging of healthy controls (n=42), in the exemplary patient and in the exemplary patient with the nasal plug according to principles of the present invention.
Figure 9C:
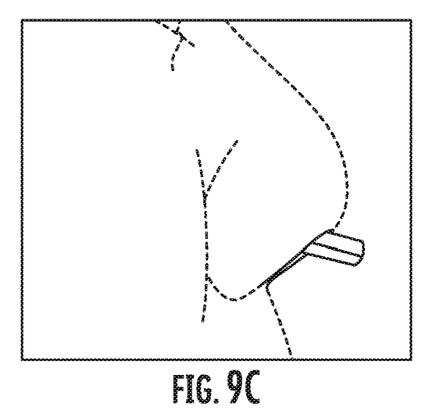
FIG. 9C illustrates the tube angle/angle of airflow in the exemplary patient.
Figure 9D:
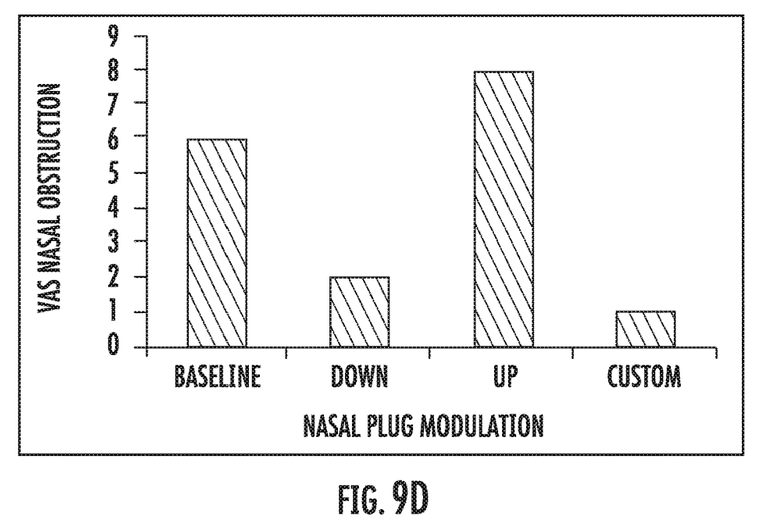
FIG. 9D illustrates scores by exemplary patient using the visual analog scare (VAS) nasal obstruction score (0 being completely free of obstruction; and 10 being completely obstructed).
Figure 9E:
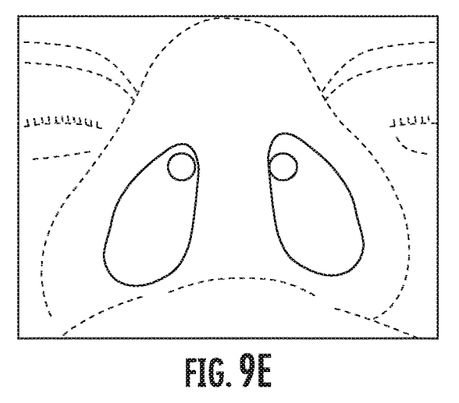
FIG. 9E illustrates the chosen custom alignment position of the exemplary patient.

The nasal plugs described herein may also be used to provide relief for patients with turbinate hypertrophy, in which a patient's turbinates are enlarged. In turbinate hypertrophy, a patient has a higher nasal resistance. The patient may experience congested or blocked breathing, sinus infections and trouble breathing at night and snorting. FIG. 9A shows the nasal cavity of an exemplary patient with turbinate hypertrophy. FIG. 9B illustrates the degree of nasal resistance averaged over 42 healthy controls, in the exemplary patient and in the exemplary patient with the nasal plug according to principles of the present invention. FIG. 9C illustrates the tube angle/angle of airflow in the exemplary patient. FIG. 9D illustrates scores by exemplary patient using the visual analog scare (VAS) nasal obstruction score to rate the performance of the nasal plug at various alignments (baseline (no plug), down, up and custom) to treat the symptoms of nasal obstruction, where 10 is complete obstruction and 0 is completely free of obstruction. FIG. 9E illustrates the chosen custom alignment position of the exemplary patient. It is expected that the 30-40% of patients with turbinate hypertrophy could experience relief with a nasal plug according to principles described herein. It is expected, but not necessary, that such patients would rotate the plug so that the airflow will be directed towards the septum or to the cavity wall.

Figure 10:
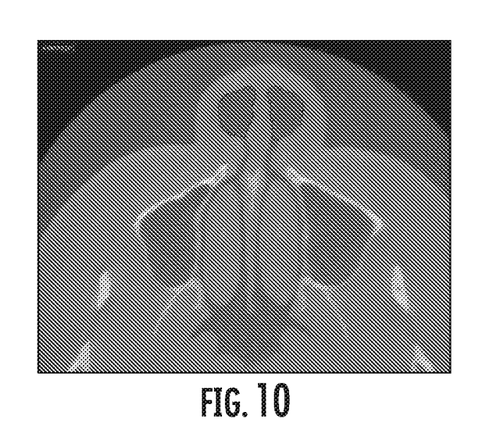
FIG. 10 shows a CT scan of a nasal cavity of a patient having disoriented airflow.
Figure 11:
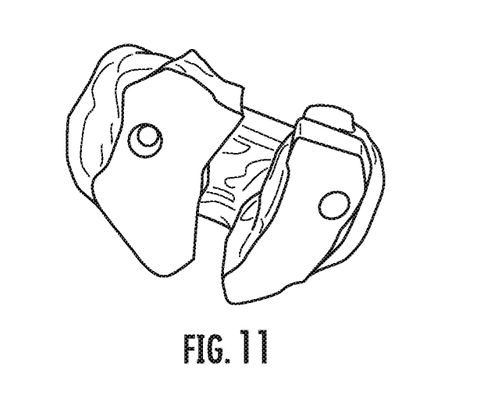
FIG. 11 is an image of a computer-modeled nasal plug according to principles of the present invention.

A nasal plug according to principles of the present invention may be custom made to fit a particular patient using various molding and manufacturing technologies. FIG. 10 shows a CT scan of a nasal cavity of a patient having disoriented airflow. FIG. 11 is an image of a computer-modeled nasal plug according to principles of the present invention that includes two nostril fittings, each nostril fitting including a passage there through from a distal end to a proximal end, where the proximal end is intended to be inserted into the patient's nostrils.

This unitary nasal plug may include tubes or other a support structure through each passage to provide additional stability and to maintain the passage or bore through the nasal plug. Such support structure can be integral or fixedly attached to the interior of the nasal plug passage or may be held in place by other methods, such as interference fit or friction fit, or may even be held in place by an adhesive. Although illustrated as cylindrical, the tube may be of any shape that provides appropriate airflow through the passage. The unitary nasal plug may be made of an elastomer, or other pliable materials, to provide a substantial seal in a person's nasal nare (s).

Figure 12:
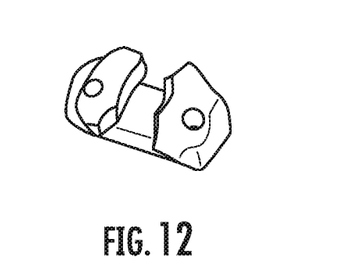
FIG. 12 shows a nasal plug made by 3D printing according to principles of the present invention.
Figure 13:
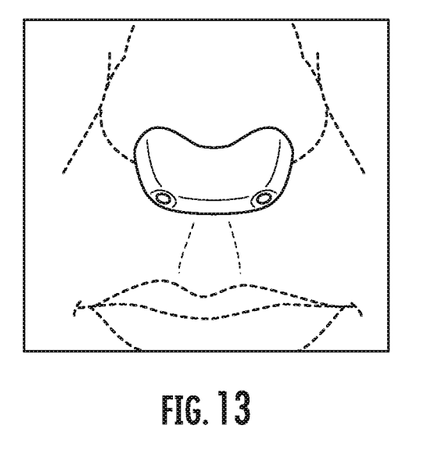
FIG. 13 shows a patient wearing a nasal plug of FIG. 12.

FIG. 12 shows a nasal plug made by 3D printing according to principles of the present invention. FIG. 13 shows a patient wearing a nasal plug of FIG. 12. A nasal plug such as that illustrated in FIG. 12 may be made by preparing a mold of a person's nostrils, which can then be used to create a negative mold for forming the nasal plug by, for example, injection molding. Alternatively, methods such as Computer Aided Design (CAD), e.g. using CT scans, could be used to form the mold, or, to prepare a nasal plug according to principles of the present invention using 3-D printing to form a highly personalized nasal plug.

As can be appreciated, this method may be used to make two separate nasal plugs, i.e., one for each of a person's nostrils.

In another aspect of the present invention, the direction of the airflow through the nasal plug may be adjusted by the patient. That is, the nasal plug may include a mechanism by which the patient may control the direction of the airflow, such providing a tube through the passage the direction of which can be adjusted by moving the tube manually from the distal end. Controlling the direction causes diversion of the airflow from its natural flowpath. In the above described foam plug, such adjustability can be provided by rotation of the plug. The tube itself may further provide a "channeling" of the airflow through the tube to facilitate the diversion of the flow path. The channeling may affect the flow rate and the volume of air entering the nostril over time.

As described herein, a nasal foam plug (which may be disposable) or a 3D-printed nasal plug that serve to re-direct nasal airflow. The foam plug is provides a simple approach for general population. A 3D printed plug is CT based that will fit each patient well, but be more expensive to make and may be distributed by physicians or medical centers. In a clinical setting, a foam plug can be first applied to a patient to determine if the redirecting of airflow according to principles of the present invention would address the patient's nasal complaints. The plug can be rotated so that all directions of airflow can be tested, until the patient reports the most comforting direction. Thus, the expense of providing a custom plug could be avoided if the airflow redirection does not address the patient's symptoms. That is, only if the patient reports symptom relief with the foam plug would a custom nasal plug be made, for example by 3D printing or molding. The custom plug design may be based solely on the foam plug results (angle, direction, etc.) or may incorporate other design information, including CT scan results and patients' medical history.

Besides ENS patients, may different patient populations that can potentially benefit from the redirection of the nasal flow. We showed an example of turbinate hypertrophy. Other examples could be septal perforation, septal deviation, narrow nasal valve, and smell loss. Common symptoms for septal perforation i.e., patients who have with a hole in their septum, include: dry nose, crusting, pain, bleeding and whistle, usually at the back edge of the perforation. Our study has shown that is where (the back edge) the bulk airflow hit and create a lot of stress. If airflow can be directed from directly hitting the back edge of the perforation, the patient may obtain relief. Additionally, patients with other sinus issues may experience relief from redirected airflow provided by the nasal plug according to principles of the present invention. Patients and healthy people may further experience an improved sense of smell using a nasal plug or plugs according to principles of the present invention.

The nasal plugs can therefore modulate airflow in the nasal passages independently and without surgery. The nasal plugs according to principles described herein differ from prior art nasal plugs at least because the nasal plugs described herein provide directionality to the airflow through the plugs. FIG. 14 illustrates exemplary embodiments of the tube or passage through the nasal plug that where the tube imparts directionality off the center axis of the plug itself. E.g., air flowing through the tube of the nasal plug is diverted from what would be a natural flow directions trough the nostrils into the nasal passages.

Known nasals plugs do not consider the directionality of the airflow created by the use of the device and merely prevent collapse of the nostrils and/or prop open the nostrils. All of these known devices have a single angle/axis of airflow and do not have the benefit of redirecting the airflow away from a "baseline" axis/direction. As such, these prior known devices do not solve the problems that ENS patients suffer, as described in detail above, particularly with respect to the ENS6Q questionnaire.

Other symptoms may be alleviated by nasal plugs according to principles of the present invention, such as nasal dryness/coldness, nasal irritation, nasal crusting, nasal burning, nasal pain, nasal bleeding, feeling of nasal obstruction/congestion, feeling of dyspnea/suffocation, difficult breathing, asthma-like breathing, feeling of nose being too open, nasal emptiness, nose feels numb, excessive nasal airflow, disturbed/disorganized airflow, nasal inflammation, increased illnesses from damaged nasal physiology such as recurrent sinus infection; disrupted nasal cycle; hypersensitivity to volatile compounds, reduced sense of smell, impaired nasal drainage, lack of mucus/difficulty removing thick mucus/clearing, sleep deprivation/unable to sleep because of difficulty breathing; anxiety, inability to relax, Impaired concentration caused by breathing, chronic fatigue.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A nasal plug, comprising:
    a pliable insert having a first surface and a second surface, a cross-section of the pliable insert sized to be accepted into and to fluidically seal a person's nasal nare, the pliable insert having an axis therethrough from the first surface to the second surface; and
    a passage through the pliable insert from the first surface to the second surface, the passage having a distal end at the first surface and a proximal end at the second surface, wherein the proximal end of the passage is offset from a center of the second surface such that air flow in the passage from the first surface to the second surface exits the passage at the second surface at an angle $\alpha$ with respect to the axis, where $\alpha>0°$.

2. The nasal plug of claim 1, further comprising a tube through the passage.

3. The nasal plug of claim 2, wherein the passage extends from the first surface to the second surface at an angle $\beta$ in a range of approximately 5° to 70° with respect to the first surface.

4. The nasal plug of claim 3, wherein the angle $\beta$ is approximately 30°.

5. The nasal plug of claim 2, wherein the tube exits the pliable insert at an angle in a range of approximately 0° to 70° to an axial direction of the pliable insert.

6. The nasal plug of claim 2, wherein the passage extends from the first surface to the second surface at an angle in a range of approximately 10° to 90° with respect to a person's sinus wall when said insert is located in the person's nostril.

7. The nasal plug of claim 1, wherein the pliable insert comprises elastomer.

8. The nasal plug of claim 2, wherein the tube comprises plastic.

9. The nasal plug of claim 1, wherein the angle $\alpha$ is in a range of approximately 5° to 70°.

10. The nasal plug of claim 1, wherein the passage extends from the first surface to the second surface at an angle $\beta$ of approximately 30° with respect to the first surface.

11. The nasal plug of claim 1, wherein the passage extends from the first surface to the second surface at an angle $\beta$ in a range of approximately 20° to 90° with respect to a person's sinus wall when said insert is located in the person's nostril.

12. The nasal plug of claim 1, wherein the proximal end of the passage exits the pliable insert at the angle $\alpha$, wherein the angle $\alpha$ is in a range of approximately 5° to 70°.

13. The nasal plug of claim 1, further comprising an additional pliable insert connected to the pliable insert, the additional insert including an additional passage through the additional pliable insert.

14. The nasal plug of claim 13, further comprising an additional tube through the additional passage.

15. The nasal plug of claim 14, wherein the additional tube comprises plastic.

16. The nasal plug of claim 13, wherein the additional pliable insert comprises elastomer.

17. The nasal plug of claim 13, wherein the passage extends at an angle different from the additional passage.

18. A kit for reducing nasal discomfort, the kit comprising:
    a first nasal plug comprising a first pliable insert having a first surface and a second surface, a cross-section of the first pliable insert sized to be accepted into and to fluidically seal a person's nasal nare, the first pliable insert having a first axis therethrough from the first surface to the second surface; and a first passage through the first pliable insert from the first surface to the second surface, the first passage having a distal end at the first surface and a proximal end at the second surface, wherein the proximal end of the first passage is offset from a center of the second surface such that air flow in the first passage from the first surface to the second surface exits the first passage at the second surface at an angle $\alpha$ with respect to the first axis, where $\alpha_1>0°$; and
    a second nasal plug comprising a second pliable insert having a third surface and a fourth surface, a cross-section of the second pliable insert sized to be accepted into and to fluidically seal a person's nasal nare, the second pliable insert having a second axis therethrough from the third surface to the fourth surface; and a second passage through the second pliable insert from the third surface to the fourth surface, the second passage having a distal end at the third surface and a proximal end at the fourth surface, wherein the proximal end of the second passage is offset from a center of the fourth surface such that air flow in the second passage from the third surface to the fourth surface exits the second passage at an angle $\alpha_2$ with respect to the second axis, where $\alpha_2>0°$;
    wherein the first nasal plug and the second nasal plug are independently rotatable with respect to one another such that the first axis and the second axis are capable of extending in different orientations.

19. The kit of claim 18, wherein the angle $\alpha_1$ is different from the angle $\alpha_2$.

* * * * *

UNITED STATES PATENT AND TRADEMARK OFFICE
CERTIFICATE OF CORRECTION

PATENT NO. : 11,737,772 B2
APPLICATION NO. : 16/491958
DATED : August 29, 2023
INVENTOR(S) : Kai Zhao It is certified that error appears in the above-identified patent and that said Letters Patent is hereby corrected as shown below:

In the Specification

Column 1, Line 2, Below "NASAL PLUG" insert:
-- CROSS-REFERENCE TO RELATED APPLICATIONS
This application is a national stage application filed under 35 U.S.C. §371 of PCT/US2018/021464 filed March 8, 2018, which claims priority to and benefit of U.S. Provisional patent application serial number 62/468,665 filed March 8, 2017, which is fully incorporated by reference and made a part hereof --.

In the Claims

Claim 24, Column 10, Line 47, delete "$\alpha$" and insert -- $\alpha_1$ --.

Signed and Sealed this
Twenty-sixth Day of December, 2023

*Katherine Kelly Vidal*

Katherine Kelly Vidal
*Director of the United States Patent and Trademark Office*